US007622510B2

(12) United States Patent
Arnaud

(10) Patent No.: US 7,622,510 B2
(45) Date of Patent: Nov. 24, 2009

(54) METHOD AND DEVICE FOR MAKING A DISPERSION OR AN EMULSION

(76) Inventor: Christophe Arnaud, 4, Rue Bremontier, Paris (FR) 75017

( * ) Notice: Subject to any disclaimer, the term of this patent is extended or adjusted under 35 U.S.C. 154(b) by 678 days.

(21) Appl. No.: 10/531,227

(22) PCT Filed: Oct. 15, 2003

(86) PCT No.: PCT/FR03/03035

§ 371 (c)(1),
(2), (4) Date: Apr. 13, 2005

(87) PCT Pub. No.: WO2004/035190

PCT Pub. Date: Apr. 29, 2004

(65) Prior Publication Data

US 2006/0164912 A1 Jul. 27, 2006

(30) Foreign Application Priority Data

Oct. 15, 2002 (FR) .................................. 02 12803

(51) Int. Cl.

| | |
|---|---|
| ***B01F 3/08*** | (2006.01) |
| ***B01F 11/02*** | (2006.01) |
| ***B01F 11/00*** | (2006.01) |
| *B01F 13/06* | (2006.01) |
| *A61K 8/06* | (2006.01) |

(52) U.S. Cl. ............................ 516/20; 516/21; 516/22; 516/53; 516/928; 366/127; 366/108; 514/937; 514/938; 424/401

(58) Field of Classification Search ................ 516/928, 516/53, 20, 21, 22; 366/127, 108; 514/937, 514/938; 424/401
See application file for complete search history.

(56) References Cited

U.S. PATENT DOCUMENTS

| | | | | |
|---|---|---|---|---|
| 2,949,900 | A * | 8/1960 | Bodine | 123/472 |
| 3,812,854 | A * | 5/1974 | Michaels et al. | 128/200.16 |
| 4,201,691 | A * | 5/1980 | Asher et al. | 516/928 |
| 4,253,962 | A | 3/1981 | Thompson | |
| 4,904,394 | A * | 2/1990 | Clarke et al. | 210/739 |

(Continued)

FOREIGN PATENT DOCUMENTS

| | | | |
|---|---|---|---|
| FR | 953 482 | | 12/1949 |
| WO | WO 2004/030799 | A1 * | 4/2004 |

OTHER PUBLICATIONS

Patent Abstracts of Japan vol. 0145, No. 13 (C-0777), Nov. 9, 1990 & JP 02 214537 A (Fuji Debuison Kagaku KK), Aug. 27, 1990 cited in the application abstract.

Patent Abstracts of Japan vol. 1996, No. 1, Jan. 31, 1996 & JP 07 232045 A (Reika Kogyo KK), Sep. 5, 1995 abstact.

*Primary Examiner*—Daniel S Metzmaier
(74) *Attorney, Agent, or Firm*—Young & Thompson

(57) ABSTRACT

A method and a device for making a dispersion or an emulsion (41) from at least two fluids known to be unmiscible, the fluids constituting a dispersed phase (40) and a dispersing phase (44), the dispersed phase (40) being driven through a porous body (24) into the dispersing phase (44). The invention is characterized in that the porous body (24) is vibrated by a mechanical, electrical or magnetic excitation.

14 Claims, 4 Drawing Sheets

U.S. PATENT DOCUMENTS 5,326,484 A 7/1994 Nakashima et al.
5,443,059 A * 8/1995 Koch et al. ............. 128/200.16
5,476,744 A 12/1995 Anno
6,281,254 B1 * 8/2001 Nakajima et al. ........... 516/924
6,380,264 B1 * 4/2002 Jameson et al. ............. 516/924
2004/0152788 A1 * 8/2004 Wu et al. ....................... 516/9
2006/0284325 A1 * 12/2006 Kohama et al. ...... 261/DIG. 26
2009/0062407 A1 * 3/2009 Iversen et al. ................. 516/10

* cited by examiner

METHOD AND DEVICE FOR MAKING A DISPERSION OR AN EMULSION

SUBJECT AND FIELD OF THE INVENTION

The present invention relates to a device and a method for making a dispersion or an emulsion from at least two fluids considered to be immiscible. Making a dispersion or an emulsion involves mixing two immiscible fluids in which one of these fluids (referred to as the "dispersed phase") is dispersed in the form of droplets in the other fluid (referred to as the "dispersing phase"). Many properties depend on the size of the droplets and in general the smaller and more homogeneous this size is, the more advantageous the dispersion will be: the smaller the droplets are, the more stable the dispersion will be; in the conventional case in which the dispersed phase is the carrier of an active principle, the smaller the drops are the better the distribution of the active principle will be.

PRIOR ART

In order to obtain a particular fineness of the drops, it is known to use a mechanical agitating action, in particular through the use of agitators with a turning mobile part, rotor-stator apparatus, pressure apparatus, homogenizers and other apparatus with a jet, or ultrasonic apparatus, membrane emulsification apparatus.

Agitators with a turning mobile part are the oldest ones, and their operation and mechanical effects are well known; many studies into the influence of the geometry of the containers and mobile parts, as well as the agitation speeds have been carried out. The mechanical energy delivered is very inhomogeneous and the power densities are limited. Furthermore, the mechanical effect is concentrated only the ends of the mobile part.

In rotor-stator systems, one ring is made to rotate with respect to another and the fluid to be processed is made to pass between the opposing surfaces of these two rings. The difference in speed between the rings thus creates a shear, which is optimized by reducing the distance between the two rings. There are many rotor-stator apparatus geometries, and some systems comprise several rows of rings. These systems, which are commonly used in the industry, are suitable particularly for dispersions with a high viscosity.

Pressure apparatus, homogenizers, the apparatus known by the name Microfluidizer (registered trademark) and other apparatus with a jet have enjoyed the most recent development. Their principle is to pressurize (up to 200 MPa) a fluid, which is generally a pre-dispersion, followed by rapid expansion in a suitable head, thus imparting significant mechanical energy to the fluid. Homogenizers have a head formed by an opening, a valve and impact plates. The principle of the Microfluidizer (registered trademark) is to separate the main flow and subsequently to create a collision of the secondary flows. Mention may also be made of a system based on pressurizing the dispersed phase, expanding it rapidly as a coherent jet and finally bringing it in contact with the dispersing phase. The devices based on these principles are confronted with the strength limitations of the equipment (high degree of wear, risk of breaking apparatus under high stresses). The very principle of expansion furthermore entails heating of the fluid, which may be detrimental for the final product.

Ultrasound is another way of exerting a mechanical action at the interface of the two phases. There are several types of ultrasound generators: the first, referred to as transducers, convert an oscillating electrical signal into an ultrasonic vibration; the second, referred to as whistles, convert the energy of a fluid jet into ultrasonic vibrations according to the principle of a vibrating plate or a resonant cavity.

There are several effects associated with ultrasound:

- the agitation (micro-flows) caused by the mechanical oscillations;
- the pressure variations in the medium exposed to the ultrasound;
- cavitation, the phenomenon of bubble creation, oscillation and implosion, which releases a very large amount of energy.

The advantage of such systems is that they achieve very high energy densities. Yet this energy is supplied very inhomogeneously, and the cavitation phenomenon has not yet been fully described by theory, which means that essentially empirical approaches have to be adopted for the development of devices and methods.

Another system for making emulsions is membrane emulsification: the dispersed phase is forced through a porous body and forms drops at the surface of this body, and the flow of dispersing phase at the surface of the porous body allows the drops to be entrained. The energy transmitted to the interface is limited by losses due to friction in the dispersing phase; the entrained drops are consequently of larger size (about 4 to 5 times the pore size) and a coalescence phenomenon occurs at the surface of the porous body, increasing the size of the drops and the inhomogeneity of the populations of drops. The coalescence phenomenon takes place when at least two drops formed at neighboring pores combine to form a single drop. One solution to the latter interfering phenomenon is envisaged in patent JP 2-214537. It consists in adding ultrasonic irradiation of the porous body. The wave generated by a standard washing system is transmitted by fluid means. With a medium-intensity ultrasound source the agitation created in this way inhibits coalescence, but a higher energy leads again to a standard ultrasonic dispersion machine configuration, with the mechanical losses and inhomogeneity of the effects.

More generally, all these devices have the more or less pronounced drawback of requiring a very large overall input of energy compared with the useful energy at the microscopic scale (an efficiency of less than 10%). This is explained by the fact that the mechanical energy is transmitted to the interface via the fluids, causing energy losses by fluid friction which are more than ten times greater than the useful energy. This dissipation of energy generally leads to a significant rise in temperature, or apparatus is worked to its limits in order to obtain satisfaction effects. Furthermore, the volumes into which the mechanical energy is delivered are more than $10^{-10}$ $m^3$ for actions on useful volumes (size of particles in dispersion, cells, etc.) conventionally of the order of $10^{-18}$ $m^3$. In view of the difference in scale, the devices which are used cannot ensure homogeneity of the mechanical agitation, of its effects and therefore of the product which is obtained.

SUMMARY OF THE INVENTION

It is an object of the invention to provide a method for making a dispersion or an emulsion from at least two fluids considered to be immiscible, which avoids the aforementioned drawbacks and which allows a homogeneous emulsion or dispersion with fine drops to be made.

It is also an object of the invention to provide a device carrying out this method, by exerting a mechanical action directly at the interface of the two phases, which makes it possible to obtain finer and more homogeneous dispersions with a better energy efficiency.

To this end, the invention relates to a method for making a dispersion or an emulsion from at least two fluids considered to be immiscible, said fluids constituting a dispersed phase and a dispersing phase, the dispersed phase being forced through a porous body into the dispersing phase, characterized in that said porous body is made to vibrate by excitation of a mechanical, electrical or magnetic type.

The dispersing phase preferably circulates at the exit surface of the porous body.

According to one variant of the method, the emulsion is recirculated in the porous body which becomes loaded with dispersed phase during the process.

The frequencies and/or the power of the vibrations are preferably controlled.

Advantageously, an emulsifier is added to at least one of the two phases.

The dispersed phase is preferably forced through the porous body under controlled conditions of temperature, pressure, flow rate, composition and agitation.

Advantageously, the dispersing phase circulates at the surface of the porous body under controlled conditions of temperature, pressure, flow rate, composition and agitation.

In another variant of this method, a wave in the microwave frequency range which causes heating of the porous body is superimposed on the excitation at the frequencies which generate the vibrations of the porous body.

The method preferably consists in using said dispersion or emulsion to make cosmetic, dermopharmaceutical or pharmaceutical products.

The invention also relates to a device for making a dispersion or an emulsion from at least one fluid, comprising at least:

- a porous body having a porous part through which said fluid can be forced, said porous body having a so-called internal cavity,
- a case which surrounds at least said porous part in a leak-tight fashion so as to define a so-called external cavity into which said porous part opens, it being possible to convey said fluid into said external cavity,
- characterized in that it has a system for making the porous body vibrate, which can apply vibrations directly to the porous body.

In the context of the invention, "directly" is used in the sense that the vibrations are not essentially transmitted via one of the fluids, in contrast to the prior art.

In the context of the invention, the device may be used for making a dispersion or an emulsion from two fluids considered to be immiscible or for homogenizing an emulsion or a dispersion of a single fluid.

The device preferably comprises a system for supplying said fluid, which can deliver said fluid into the external cavity under controlled conditions of temperature, pressure, flow rate, composition and agitation.

Advantageously, the device comprises a system for supplying another fluid, which can deliver this other fluid into said internal cavity under controlled conditions of temperature, pressure, flow rate, composition and agitation.

The device preferably comprises an extraction system making it possible to discharge, store or send the emulsion or the dispersion to another system, or to recirculate the emulsion or the dispersion.

According to one embodiment, the system for making the porous body vibrate consists of a winding connected to an alternating current source and surrounding the case, which is permeable to the magnetic waves generated by the winding, the porous body being made of a magnetostrictive material.

According to another embodiment, the system for making the porous body vibrate consists of a conductive rod arranged coaxially with the porous body and a conductive case, said conductive rod and said case being connected to an alternating current source, the porous body being made of a piezoelectric material.

The conductive rod and/or the surface of the porous body are preferably covered with an insulator.

According to yet another embodiment, the system for making the porous body vibrate consists of two transducers which are fixed to the ends of the porous body and are connected to an alternating current source, said transducers consisting of a piezoelectric material.

Advantageously, each transducer has a support means fixed to the case, said support means having a recess in which one end of the porous body is positioned, said support means having at least one pair of radial holes, each pair containing a piezoelectric element in one hole and a resilient application means in the other hole of the same pair, in order to keep the piezoelectric element bearing against the porous body, the holes in each pair being diametrically opposite.

The support means preferably has two pairs of holes, the two pairs of holes being arranged in perpendicular directions, and the two piezoelectric elements are supplied with signals that are offset by one fourth of a period with respect to each other and, in combination with the prestressing springs, cause displacement of the porous body in an overall circular trajectory.

BRIEF DESCRIPTION OF THE DRAWINGS

The invention will be understood more clearly and other objects, details, characteristics and advantages thereof will become more readily apparent during the following detailed explanatory description of several embodiments of the invention, which are given by way of purely illustrative and non-limiting examples, with reference to the appended schematic drawings.

In these drawings.

DESCRIPTION

In FIGS. 1, 2, 3 and 7, the device is in the form of an active module 2, 102 and 202.

Figure 1:
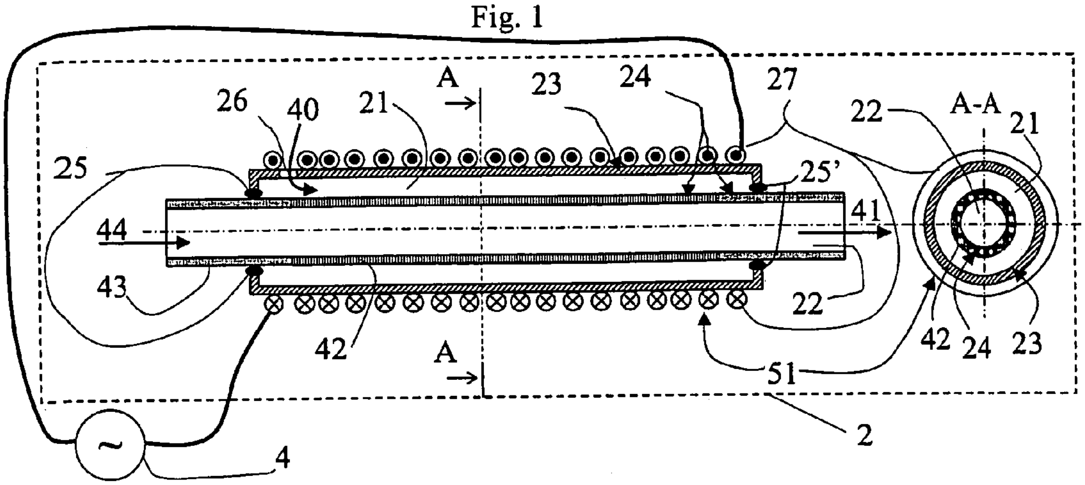
FIG. 1 represents a longitudinal section of a module containing the porous body and a magnetic excitation means, and a section along the axis A-A of this module.

In FIG. 1, this module 2 is composed of a porous body 24, a winding 27 and a case 23.

The porous body 24 is in the form of a hollow cylinder, the porous central part 42 of which is contained in the case 23 whose shape is cylindrical and coaxial with the porous body 24. The space contained between the porous body 24 and the case 23 defines an external cavity 21.

The case 23 is connected to the ends 43 of the porous body 24 by a sealing system 25 and 25'. An internal cavity 22 is also defined inside the porous body 24.

The winding 27, which is connected to an alternating current source 4 whose power and frequency are controllable, produces an oscillating magnetic field. The porous body 24 is made of a magnetostrictive material, and the case 23 is made of a material which is permeable to the magnetic waves produced by the winding 27.

The dispersed phase 40 is conveyed through the orifice 26 into the external cavity 21, then it is forced through the porous part 42 as far as the internal cavity 22, level with the so-called exit surface where it will be brought in contact with the dispersing phase 44 circulating from the left-hand end 43 of the porous body to the right-hand end. The emulsion or the dispersion 41 is based on bringing the dispersed phase 40 in the form of droplets into contact with the dispersing phase 44 after having passed through the porous body 42.

The purpose of the case 23 is to prepare the dispersed phase 40, which will be forced through the porous body 24, and facilitate the vibrations of the porous body 24 without degrading it.

The sealing system 25 and 25' may advantageously be formed by two flexible seals which provide both leaktightness and mobility of the porous body with respect to the case 23.

The embodiment represented in FIG. 1 is a system 51 for vibration by magnetic excitation, i.e. the system 51 is formed by the alternating current source 4 connected to the winding 27, the geometry of which makes it possible to exert an alternating magnetic field on the porous body 24.

The porous body 24, thus exposed to an oscillating magnetic field, vibrates and exerts the intended mechanical action on the interface of the two phases 40 and 44. Owing to this mechanical action produced at the interface of the phases 40 and 44, the droplets thus formed are rapidly separated from the pore from which they originate and become mixed into the dispersing phase 44 with a very small droplet size.

Figure 2:
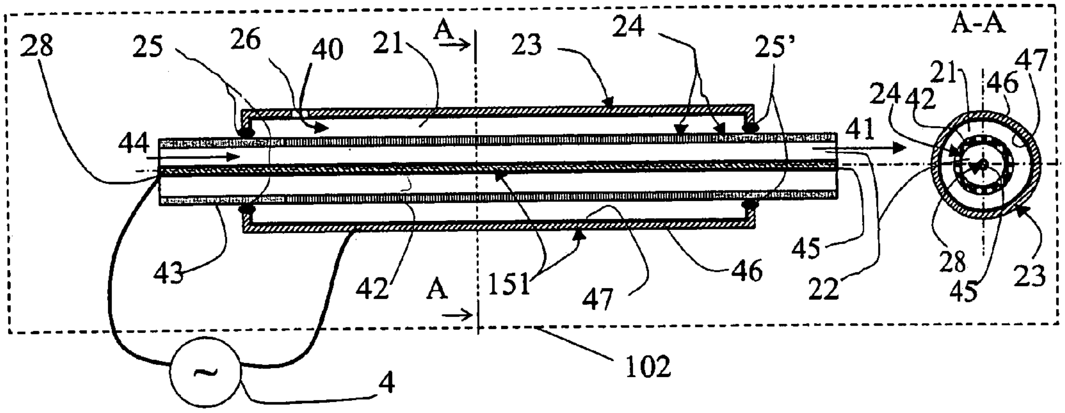
FIG. 2 is a longitudinal section of a module containing the porous body and an electrical excitation means, and a section along the axis A-A of this module.

The embodiment represented in FIG. 2 illustrates a system 151 for vibration by electrical excitation.

Those elements which are the same will be given the same references and will not be described again.

The active module 102 differs from that presented in FIG. 1 only by the vibration system.

The vibration system 151 now comprises an alternating current source 4 connected to conductive surfaces, between which the porous body 24 is placed.

The conductive surfaces consist of the conductive layer 46 of the case 23 and a conductive rod 28 placed coaxially with the cylinder formed by the porous body 24. Each of the conductive surfaces 46 and 28 is connected to a terminal of an alternating current source 4 whose power and frequency are controllable, so as to create an oscillating electric field.

The conductive rod 28 is made of a conductive material advantageously covered with an insulating layer 45, and the case 23 likewise comprises at least one conductive layer 46 advantageously covered with an insulator 47 (represented by the thick black line defining the contour of the external cavity 21).

When subjected to this field, the porous body 24 made of a piezoelectric material vibrates and thus exerts the intended mechanical action at the interface of the dispersed phase 40 and the dispersing phase 44.

Figure 3:
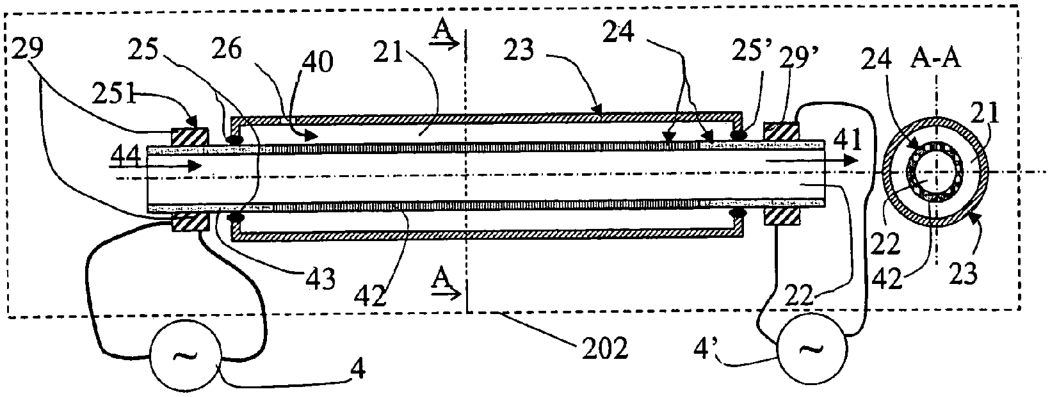
FIG. 3 is a longitudinal section of a module containing the porous body and a mechanical excitation means, and a section along the axis A-A of this module.

The embodiment represented in FIG. 3 illustrates a system 251 for vibration by mechanical excitation.

Those elements which are the same will be given the same references and will not be described again.

The active module 202 differs from that presented in FIGS. 1 and 2 only by the vibration system.

The vibration system 251 now comprises an alternating current source 4 and 4' connected to one or more mechanical vibrators (mechanical linkage) coupled with the porous body 24, which may advantageously be transducers 29 and 29' in the form of a collar fixed to the ends 43 of the porous body 24.

These transducers 29 and 29' transmit the vibrations directly to the porous body 24. The system formed by the transducers 29 and 29' and the porous body 24 in this case forms an oscillator, thus exerting the intended mechanical action at the interface of the dispersed phase 40 and the dispersing phase 44.

Figure 7:
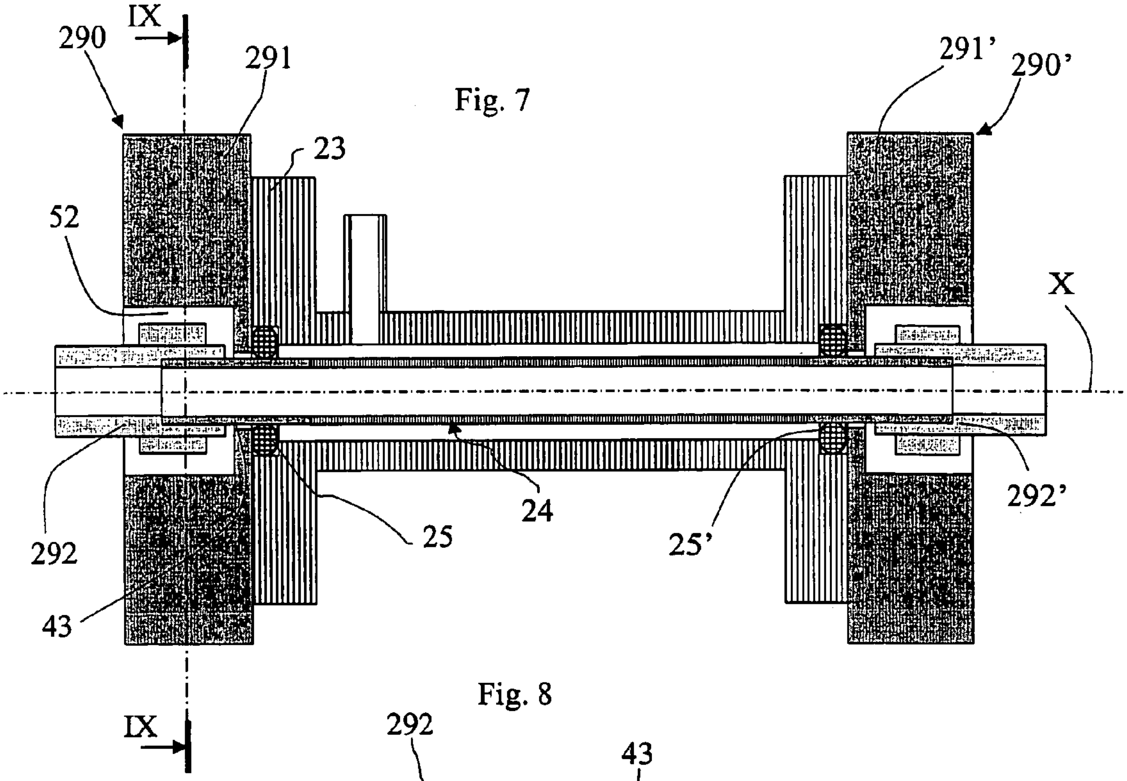
FIG. 7 is a longitudinal section of a module containing the porous body and a mechanical excitation means according to a second embodiment.
Figure 9:
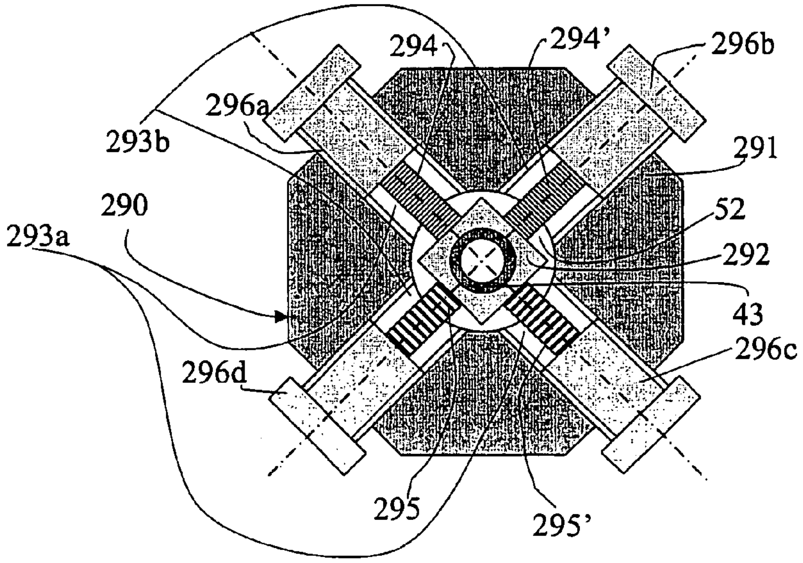
FIG. 9 is a section along the axis IX in FIG. 7 of a module containing the porous body and a mechanical excitation means.

A particular embodiment of the transducers 290 and 290' in the form of a collar is represented in FIGS. 7 and 9.

According to FIG. 7, the transducers 290 and 290' are placed level with each end 43 of the porous body 24, such that they are fixed against the case 23 and the sealing system 25 and 25'.

The transducers 290 and 290' are formed by a support means 291 and 291', for example in the form of an octagonal collar containing a recess 52 coaxial with the axis X and, according to FIG. 9, two radial tapped holes **293*a* and 293*b*. The end 43 of the porous body 24 is fitted into a connecting sleeve 292 or 292', which is itself placed in the coaxial recess 52**.

Figure 8:
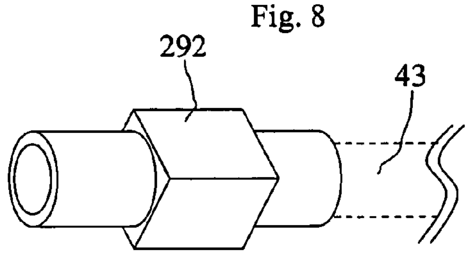
FIG. 8 is a perspective view of a connecting sleeve.

According to FIG. 8, this connecting sleeve 292 is formed by a hollow cylinder passing through a cube whose width is greater than the external diameter of the cylinder level with its central portion, i.e. level with the central portion of the sleeve 292 the cross section is in the form of a square circumscribing a circle that corresponds to the internal diameter of the cylinder. The end 43 of the porous body 24 is placed fixed in the sleeve 292, so that the sleeve 292 transmits the movement applied to it to the porous body 24.

According to FIG. 9, each hole **293*a* and 293*b* is fitted with a piezoelectric element 294 and a prestressing spring 295 on either side of the connecting sleeve 292. Four adjusting screws 296*a*, 296*b*, 296*c* and 296*d* close the ends of each hole 293*a* and 293*b*. The prestressing springs 295 are precompressed by means of the aforementioned four screws 296*a*, 296*b*, 296*c* and 296*d***.

The piezoelectric elements 294 are supplied with two periodic electrical signals in quadrature with respect to each other (i.e. an offset of one fourth of a period) and experience an elongation proportional to the supply voltage. They act in traction and in compression perpendicularly to the axis of the porous body 24, thus generating vibration modes of the ends 43 of the porous body 24 which cause it to flex. Since the input signal is rarely pure, i.e. it contains other secondary signals at other frequencies in addition to the main signal at a given frequency, the movements then described by the cross sections of the porous body 24 are made up of a sum of circular trajectories (each corresponding to one frequency of the input signal), guaranteeing an overall circular trajectory over a section. The two input signals on the two piezoelectric elements are furthermore identical to within one fourth of a period, so as to ensure that each point of the porous body 24 level with a given cross section experiences the same vibrations and thus to guarantee homogeneity of mechanical action.

The transducers 290 and 290' are supplied with signals of different frequencies, each corresponding to one natural mode of the system. This allows optimization and good control of the generation of the vibrations, while avoiding vibration nodes where the mechanical action would be absent.

Figure 4:
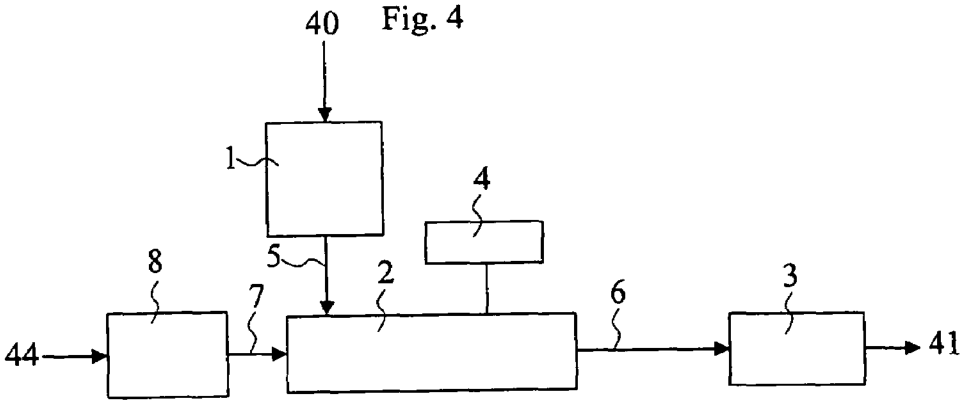
FIG. 4 is a schematic representation of one embodiment of the invention.

In the embodiment of the invention represented in FIG. 4, the device comprises an active module 2 connected via the pipeline 5 to the supply system 1 of the dispersed phase 40, via the pipeline 7 to the supply system 8 of the dispersing phase 44, and via the pipeline 6 to the extraction system 3. The active module 2 is also connected to an alternating current source 4.

The alternating current source 4 provides the active module 2 with the energy needed to generate the mechanical action necessary for generating fine droplets. The extraction system 3, which is connected to the active module 2 via the pipeline 6, makes it possible to discharge the emulsion or the dispersion 41 from the porous body 24.

Figure 5:
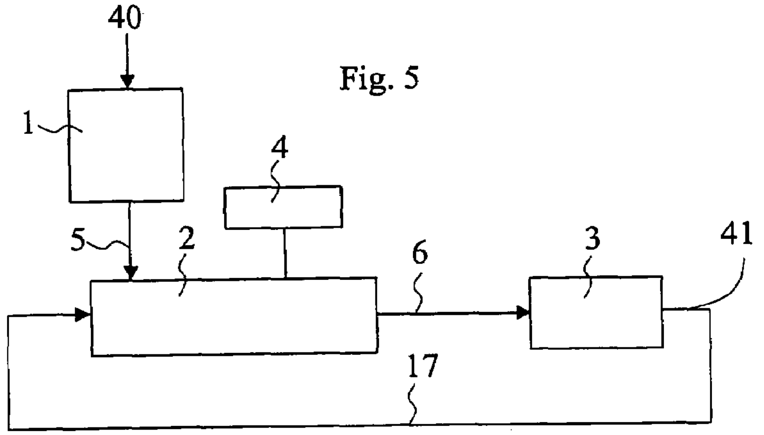
FIG. 5 is a schematic representation of an embodiment of the invention with recirculation of the emulsion or the dispersion.

A variant of this embodiment, which is represented in FIG. 5, comprises the same elements as in the previous embodiment except that a pipeline 17 connects the extraction system 3 to the module 2. The extraction system 3 then allows the emulsion or the dispersion 41 to be returned, thus creating a recirculation.

Figure 6:
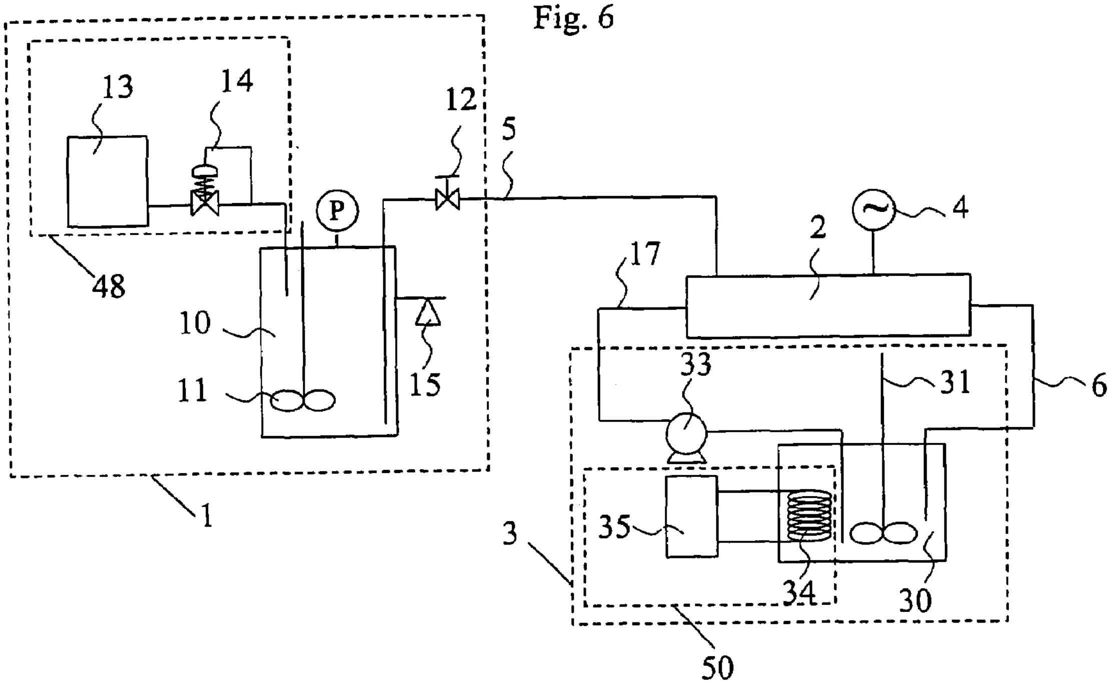
FIG. 6 is a detailed schematic representation of the device presented in FIG. 5.

In this alternative embodiment, according to FIG. 6, the extraction system 3 is formed by at least one reservoir 30 and a pump 33 located between this reservoir 30 and the pipeline 17. The reservoir 30 is provided with an agitation system 31 and with a temperature maintenance system 50, formed by a thermostatted bath 35 and an exchanger coil 34.

The supply system 1 of the dispersed phase 40 comprises a pressurized gas supply 48 formed by a reservoir 13 (bottle under pressure or compressor coupled to an expansion vessel) and an expander 14. The system 1 also comprises a pressurizable reservoir 10 for the dispersed phase 40, which is provided with an agitation system 11 and is mounted on scales or a balance 15. Lastly, the system 1 comprises a shutoff valve 12.

The expander 14 makes it possible to set the pressure at which the dispersed phase 40 is forced through the supply system 1.

The scales or a balance 15 are used to control the mass and the flow rate of dispersed phase 40 injected into the supply system 1.

APPLICATION EXAMPLE

An exemplary embodiment of the invention will now be described by way of a nonlimiting example.

The active module which is used corresponds to that represented in FIG. 3, with an embodiment identical to that in FIG. 6.

The active module may advantageously be a monochannel tangential filtration module suitable for the application, using porous bodies of hydrophilic ceramic with a pore diameter of 0.1 μm and 0.8 μm. A hollow cylindrical porous body with a length of between 20 and 30 mm, an outer radius of between 10 and 15 mm and an inner radius of between 7 and 12 mm will be used.

The exemplary embodiment relates to making an emulsion 41 of the oil in water type, for example formed by 10% soy oil, 0.5% Tween 20 (registered trademark) emulsifier and 89.5% water.

A mixture of 4.8% Tween 20 and 95.2% oil is made in the reservoir 10 under agitation. A quantity X of water is then circulated from the reservoir 30. Once the valve 12 has been closed, the expander 14 is set to a pressure of between 0.1 and 5 bar. The transducers 29 and 29' are supplied independently by the alternating current source 4 (formed by two separate sources) with signals of powers between 0 W and 2 kW and two frequencies, one of which is between 14 and 16 kHz and the second between 18 and 22 kHz. The valve 12 is then opened, and re-closed when the quantity of oil+emulsifier mixture reaches 0.1173×. Throughout the operation, the temperature is maintained around a setpoint temperature of between 15 and 25° C.

Figure 10:
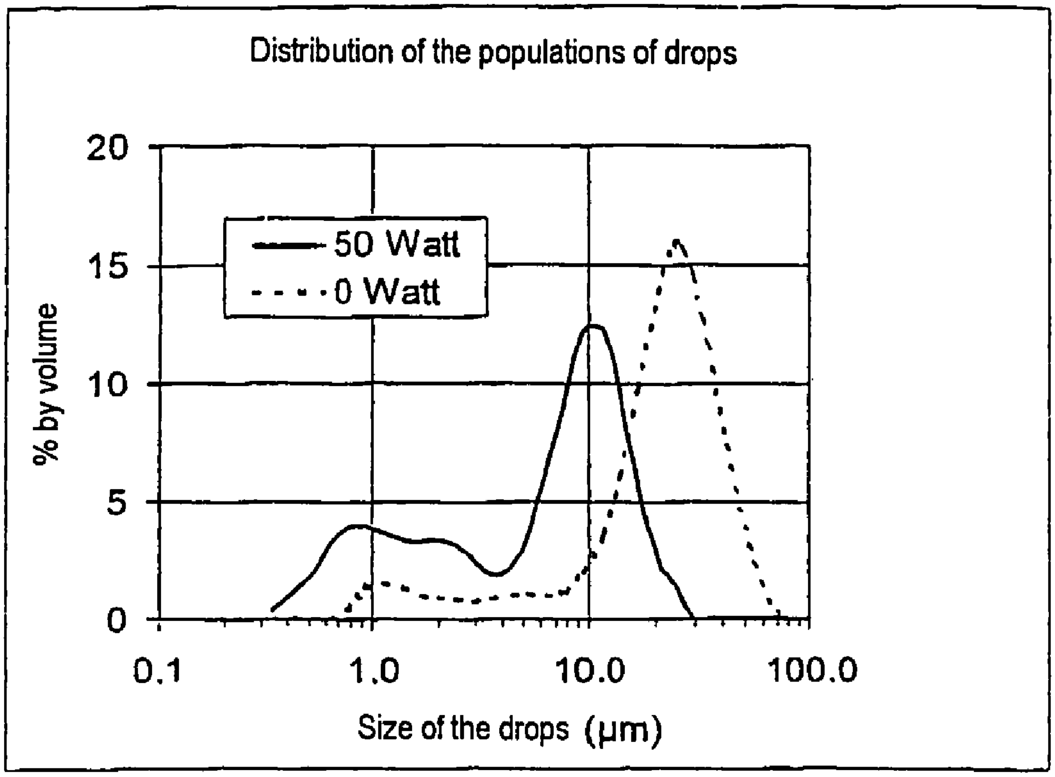
FIG. 10 is a diagram presenting the results of the application example.

In order to verify the contribution of the vibrations to the intended technical effect, the same experiment is carried out without vibration. The volume distributions of the drop sizes of the emulsions obtained with or without vibrations are then measured using a Malvern (registered trademark) laser diffraction granulometer. The results of the measurements for a porous body 24 with a pore size of 0.8 μm with and without vibrations generated by a power of 50 W are illustrated in FIG. 10, the diagram presenting the volume percentage of the populations of drops as a function of their size (on a logarithmic scale). The distribution of the populations is represented by a broken line for the test without vibration and with a continuous line for the test with vibrations. The presence of several populations of drops, identified by several peaks, can be seen each time. The presence of these same drop populations was confirmed by images taken with an electron microscope (these images are not shown).

A high population proportion with a large size is observed in the case when no vibration is applied (more than 15% by volume), which seems to be due to the coalescence phenomenon. Furthermore, a significant reduction of this proportion is observed (about 12% by volume) with the use of vibrations. The use of vibrations thus seems to inhibit coalescence. A shift of the peaks toward smaller size values can furthermore be seen (30 μm for the tests without vibration and 10 μm for the tests with vibrations) which seems to indicate that the vibrations facilitate formation and detachment of the drops. It also appears that the vibrations facilitate the flow of dispersed phase through the porous body 24, because differences of 10% were observed during the tests. These hypotheses should not, however, in any way be regarded as limiting the invention.

Furthermore, an emulsion 41 whose drop size is less than 300 nm is obtained with an electrical power of 200 W and a porous body 24 with a pore diameter of 0.1 μm (these results are not shown).

It may, in particular, be fruitful to apply this example to making cosmetic, dermopharmaceutical or pharmaceutical products.

In the detailed description of the drawings given above, distinction will have been made between three systems for making the porous body vibrate: by mechanical excitation 251, electrical excitation 151 or magnetic excitation 51. These various systems 51, 151 and 251 may be coupled for an optimum effect. It should also be noted that distinction was made between the two principles in the case of magnetic and electrical excitations. According to Maxwell's equations, however, the generation of an oscillating magnetic field entails the generation of an oscillating electric field (and vice versa), thereby coupling the two effects.

The vibrations of the exit surface of the porous body 24 act in this invention to release disruptive mechanical energy directly at the interface of the dispersed phase 40 and the dispersing phase 44, making it possible to avoid the formation of large drops and causing the formation of fine drops of dispersed phase 40 in the dispersing phase 44 on which the emulsion 41 is based.

The system thus makes it possible to transmit a large amount of energy to the interface of the two phases 40 and 44, since this transmission takes place through a solid (the porous body 24) rather than through the fluids. It seems that under these conditions, the coalescence phenomena are inhibited and the formation and detachment mechanism of the drops is accelerated. This hypothesis should not, however, in any way be regarded as limiting the invention.

The choice of the vibration mode dictates the magnetostrictive, piezoelectric or electrostrictive properties of the porous body. Other geometrical, mechanical, physicochemical and chemical properties are determined by the application.

The overall shape of the porous body 24 should make it possible to optimize the surface through which the dispersed phase 40 passes, while facilitating the transmission or generation of vibrations. One of the shapes, the hollow cylinder (which adopts the layout principle of a tangential filtration membrane), is the one presented above. Mention may also be made of a solid cylinder placed in a pipeline with the dispersed phase flowing along the axis of the cylinder, or alternatively a plug which is fixed in a pipeline and whose exit surface is flush with the inner surface of an agitated vessel. The porosity, the size of the pores and the thickness of the porous body 24 determine the effective volume and the duration of the mechanical action. The mechanical strength and elasticity affect the amplitude of the vibrations and therefore the intensity of the mechanical action. The hydrophilic/hydrophobic nature can substantially modify the paths of the fluid through the body, as well as the porous body 24//dispersed phase 40//dispersing phase 44 interface (contact angle). A body 24 having a good affinity with the dispersing phase 44 is therefore advantageously chosen so as to promote detachment of the drops of dispersed phase 40. It is also necessary for the selected materials to be compatible with the products being used. If a body which is not permeable to microwaves is used, it is impossible to heat this body and to supplement the mechanical affect with a thermal effect.

In general, it will be noted that the porous body 24 is not necessarily homogeneous. For example, a porous body 24 may be selected in which only the layer in contact with the dispersing phase 44 has a suitable porosity, the rest of the body 24 being used as a support for this layer. Likewise, in order to ensure the leaktightness necessary for the forced passage of the dispersed phase 40 through the porous body 24, a part of the body 24 located at its ends 43 may be non-porous. The properties of the porous body 24, and consequently its composition and its treatment, are thus defined according to the application.

Although the invention has been described with reference to several particular embodiments, it is clear that it is in no way limited to them and that it covers all the technical equivalents of the described means as well as their combinations so long as these lie within the scope of the invention.

The invention claimed is:

1. A method for making an emulsion (41) from at least two liquids, said liquids constituting a dispersed phase (40) and a dispersing phase (44), comprising:

forcing said dispersed phase (40) from a surrounding portion of a cylindrical porous body through the cylindrical porous body (24) into the dispersing phase (44) within the inner hollow portion of the cylindrical porous body (24), wherein a mechanical excitation system (251) makes the porous body (24) vibrate by applying vibrations directly to said porous body (24), and the mechanical excitation system (251) acts in traction and in compression perpendicularly to an axis of the porous body (24).

2. The method as claimed in claim 1, wherein the dispersing phase (44) circulates at an exit surface of the porous body (24).

3. The method as claimed in claim 2, wherein the emulsion (41) is recirculated in the porous body (24), which becomes loaded with the dispersed phase (40) during the method.

4. The method as claimed in claim 1, wherein frequencies and/or power of the vibrations are controlled.

5. The method as claimed in claim 1, wherein an emulsifier is added to at least one of the two phases (40, 44).

6. The method as claimed in claim 1, wherein the dispersed phase (40) is forced through the porous body (24) under controlled conditions of temperature, pressure, flow rate, composition and agitation.

7. The method as claimed in claim 1, wherein the dispersing phase (44) circulates at a surface of the porous body (24) under controlled conditions of temperature, pressure, flow rate, composition and agitation.

8. The method as claimed in claim 1, wherein said emulsion (41) forms cosmetic, dermopharmaceutical or pharmaceutical products.

9. The method as claimed in claim 1, in which said mechanical excitation system (251) comprises two transducers (29, 29') which are fixed to ends (43) of the porous body (24) and are connected to an alternating current source (4), said transducers (29, 29') being formed from a piezoelectric material.

10. The method as claimed in claim 9, in which each transducer (290, 290') has a support means (291) fixed to a case (23), said case (23) surrounding at least the porous body (24) in a leak-tight fashion so as to define an external cavity (21) into which said porous part (24) opens, said support means (291) having a recess (52) in which one end (43) of the porous body (24) is positioned, said support means (291) having at least one pair of radial holes (293*a*, 293*b*), each pair containing a piezoelectric element (294) in one hole and a resilient application means (295) in the other hole of the same pair (293*a*, 293*b*), in order to keep the piezoelectric element (294) bearing against the porous body (24), the holes (293*a*, 293*b*) in each pair being diametrically opposite.

11. The method as claimed in claim 10, in which the supports means (291) has two pairs of holes (293*a*, 293*b*), the two pairs of holes (293*a*, 293*b*) being arranged in perpendicular directions, and the two piezoelectric elements (294) are supplied with signals that are offset by one combination with prestressing springs (295), cause displacement of the porous body (24) in an overall circular trajectory.

12. The method as claimed in claim 1, in which the porous body (24) has a better affinity with the dispersing phase (44) than with the dispersed phase (40).

13. The method as claimed in claim 1, in which the emulsion obtained has a drop size less than 300 nm.

14. A method for making an emulsion (41) from at least two liquids, said liquids constituting a dispersed phase (40) and a dispersing phase (44), comprising:

forcing said dispersed phase (40) through a porous body (24) into the dispersing phase (44), wherein an excitation system (251) makes the porous body (24) vibrate by applying vibrations directly to said porous body (24), wherein a wave in a microwave frequency range, which causes heating of the porous body (24), is superimposed on an excitation at frequencies which generate the vibrations of the porous body.

* * * * *

UNITED STATES PATENT AND TRADEMARK OFFICE

CERTIFICATE OF CORRECTION

PATENT NO. : 7,622,510 B2
APPLICATION NO. : 10/531227
DATED : November 24, 2009
INVENTOR(S) : Christophe Arnaud It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1260 days.

Signed and Sealed this

Fourteenth Day of December, 2010

David J. Kappos
*Director of the United States Patent and Trademark Office*